United States Patent [19]

Smith et al.

[11] Patent Number: 5,101,679

[45] Date of Patent: Apr. 7, 1992

[54] SCREW DRIVE ENGAGEMENT/DISENGAGEMENT AND DECOUPLING MECHANISM

[75] Inventors: Eugene P. Smith, Westminster; Robert R. Boyd, Arvada, both of Colo.

[73] Assignee: IVAC Corporation, San Diego, Calif.

[21] Appl. No.: 461,658

[22] Filed: Jan. 8, 1990

[51] Int. Cl.⁵ .............. F16H 29/20; F16H 27/02; A61M 5/00

[52] U.S. Cl. .............. 74/424.8 A; 74/424.8 R; 74/89.15; 604/155; 128/DIG. 1

[58] Field of Search .............. 128/DIG. 1; 604/155; 74/424.8 A, 424.8 R, 89.15

[56] References Cited

U.S. PATENT DOCUMENTS

| | | | |
|---|---|---|---|
| 3,235,220 | 2/1966 | Räntsh et al. | 74/424.8 A X |
| 3,757,591 | 9/1973 | Taylor | 74/424.8 A X |
| 3,842,690 | 10/1974 | Gulick | 74/424.8 A X |
| 3,858,581 | 1/1975 | Kamen | 128/218 |
| 3,886,938 | 6/1975 | Szabo et al. | 128/218 |
| 4,023,431 | 5/1977 | Pavlas | 74/424.8 A |
| 4,125,049 | 11/1978 | Price, Jr. | 74/424.8 A X |
| 4,424,720 | 1/1984 | Bucchianeri | 74/89 |
| 4,435,173 | 3/1984 | Siposs et al. | 609/155 |
| 4,465,474 | 8/1984 | Mardorf et al. | 604/154 |
| 4,479,398 | 10/1984 | Watanabe | 74/89.15 |
| 4,804,368 | 2/1989 | Skakoon et al. | 128/DIG. 1 X |
| 4,932,279 | 6/1990 | Kasuga | 74/89.15 X |

*Primary Examiner*—Allan D. Herrmann
*Assistant Examiner*—Julie Krolikowski
*Attorney, Agent, or Firm*—Fulwider Patton Lee & Utecht

[57] ABSTRACT

A half-nut block containing a threaded bore and a larger, overlapping, unthreaded bore is engaged with a lead screw. The larger bore overlaps the threaded bore so that effectively a half-nut results. The half-nut comprises a face having an acute angle in relation to the lead screw and this angled face contacts the inside of a bearing block within which the half-nut is mounted. The bearing block is slidably mounted on a C-tube which is mounted around and extends along a predetermined length of the lead screw. Also mounted on the C-tube is an arm for transmitting the linear motion of the bearing block to a remote point such as the plunger of a syringe. The arm is coupled to the bearing block at points selected so that transmission to the arm of any wobbling of the bearing block is reduced. The arm includes a lever which engages a cam formed on the half-nut to force the half nut to disengage from the lead screw when the arm is to be moved to a new location on the lead screw. A spring bias is coupled to the half-nut block opposite the cam for urging the half-nut block back into contact with the lead screw after disengagement. A stop mechanism prevents undesired disengagement of the half-nut block from the lead screw when force is applied other than by the cam block.

27 Claims, 3 Drawing Sheets

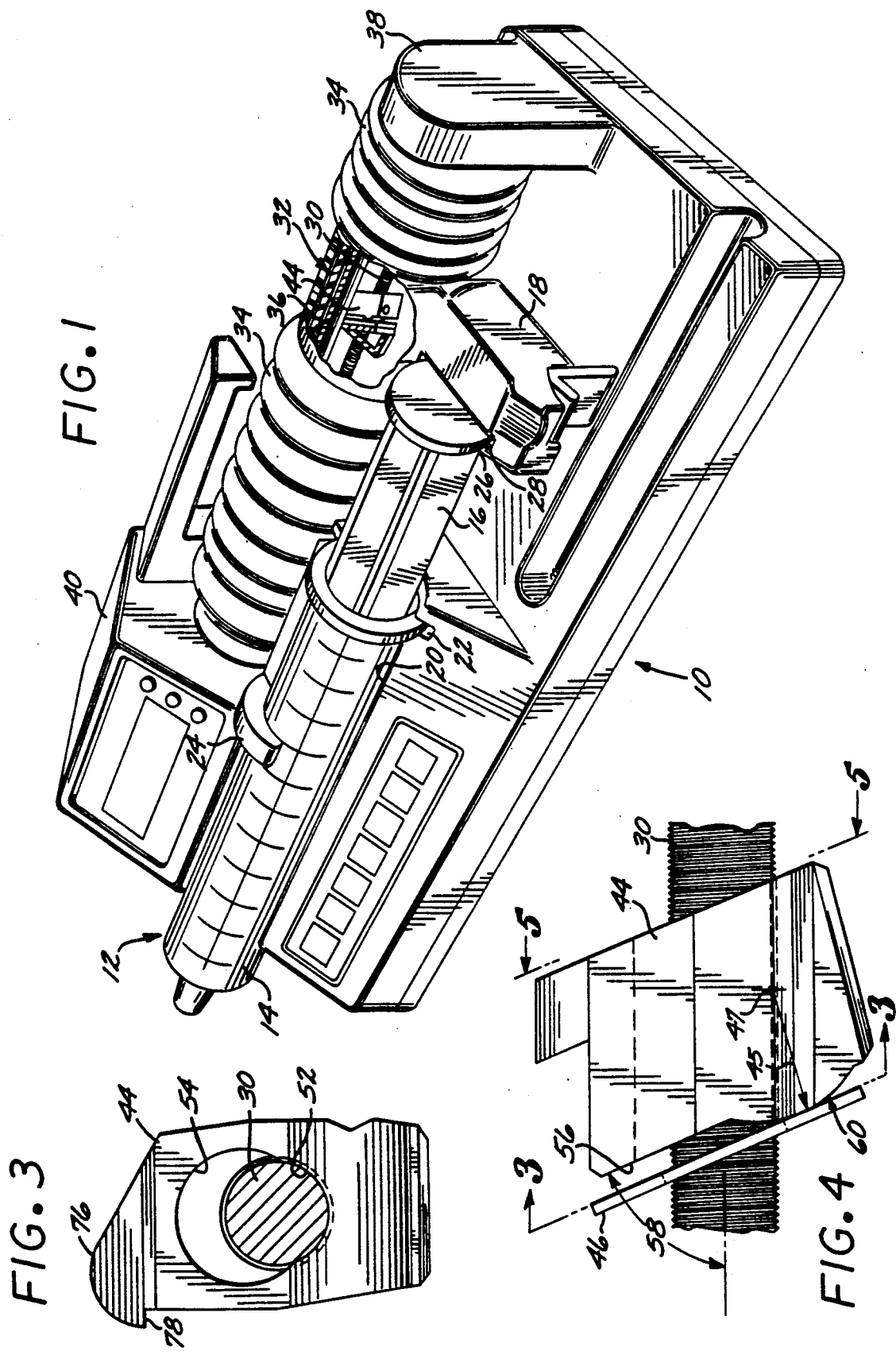

SCREW DRIVE ENGAGEMENT/DISENGAGEMENT AND DECOUPLING MECHANISM

BACKGROUND

The invention relates generally to screw drive mechanisms and more particularly, to a new and improved mechanism for use in pumps, such as a syringe pump, requiring the engagement and disengagement with a lead screw for use in coupling the pump to a device for the administration of medical fluids.

In the field of syringe pumps which are used for dispensing medical fluids at an accurate rate and in some cases, at a slow and accurate rate, some designs have used lead screws. Typically, a nut or traveler mechanism is engaged with the lead screw and moves along the lead screw in accordance with the rotation thereof. Coupled to the traveler mechanism and moving therewith is typically an arm which is also coupled to the plunger of the syringe to apply pressure to the plunger which in turn applies pressure to the fluid contained in the syringe for the delivery thereof.

In many cases, self-contained syringes are used. These syringes are pre-loaded with varying amounts of fluid and the syringe plunger may be in any position. The syringe pump arm must be movable along the lead screw to accommodate these preloaded syringes. One prior technique for positioning the arm used the rotation of the lead screw itself to position the arm prior to syringe installation. Because such a technique is based on trial-and-error for correct placement, it could be very time consuming.

Another prior approach employs a traveler mechanism having a half-nut mounted on the lead screw. Upon loading a new syringe, the half-nut is moved away from the lad screw so as to disengage from the lead screw threads, moved to the proper position and moved back into engagement with the lead screw. Various techniques have been developed for assuring that the half-nut of the traveler mechanism remains in contact with the lead screw during the engaged mode. In the cases of tightly fitting syringe plungers or viscous fluids in the syringe and which require considerable force to move the plunger, the half-nut must be held against the lead screw with sufficient force so that undesired disengagement does not occur during the development of the force required to pump the syringe contents. In one prior approach, a spring was used to exert considerable pressure on the half-nut to retain its contact with the lead screw threads. This pressure can have the effects of excessive lead screw and half-nut thread wear as well as deformation of the lead screw, such as bowing.

Another problem encountered with prior half-nut techniques is the transmission and in some cases the amplification of the imperfections in the lead screw to the arm mechanism. For example, lead screws having threads following a varying helix or which are otherwise non-uniform around the screw will cause a "wobbling" of the traveler mechanism. This wobbling can be amplified by the moment of the arm which is coupled to the syringe plunger. Such wobbling may cause uneven pressure on the fluid in the syringe which results in flow variations and inaccuracy. While it may be possible to manufacture more accurate lead screws, their cost would be higher.

Hence, it would be an advantage to provide a traveler mechanism which is disengagable from the lead screw threads so that it may be positioned along the lead screw as desired, which does not require a large spring to provide force to retain the contact between the half-nut and the lead screw, and which provides a means of decoupling undesired motion of the lead screw from the arm so that transmission of lead screw imperfections to the arm is reduced.

SUMMARY OF THE INVENTION

Briefly, and in general terms, the present invention resides in a new and improved mechanism for lead screw engagement and disengagement and for decoupling. A traveler mechanism for traveling along the lead screw includes a half-nut block having first and second bores, the first bore having threads and being of a size such that it is capable of engaging the lead screw threads. The second bore being larger than and partially overlapping the first bore and being threadless. The overlapping position of the second bore is chosen so that first bore is effectively a half-nut. The second bore is of a larger diameter than that of the lead screw such that when the lead screw is centered within the second bore, the lead screw and the half-nut block will not touch each other. In one embodiment, the half-nut block has an exterior, rounded surface, a tangent to which would be disposed at an acute angle to the lead screw when the half-nut block is engaged therewith. A bearing surface on this rounded surface contacts an angled surface disposed inside a bearing block which is also part of the traveler mechanism and in which the half-nut block is mounted. The bearing block of the traveler mechanism is mounted on a "C"-tube which extends along at least part of the length of the lead screw and partially surrounds it. Thus the bearing block can only travel in a direction parallel with the lead screw. This arrangement results in a biasing system which tends to keep the half-nut block in contact with the threads of the lead screw. Because of the angled surface of the bearing block which contacts the half-nut block and the restriction that the bearing block can only travel in a direction parallel to the lead screw, the very movement of the half-nut block by means of rotation of the lead screw causes the half-nut block to develop a force into the lead screw threads. The angle of this bearing block angled surface is selected to develop enough force in the half-nut block to overcome frictional forces between the half-nut block and the angled surface of the bearing block and to drive the half-nut block into the threads of the lead screw. The location of the rounded surface on the half-nut block is selected to result in uniform distribution of the forces across all of the lead screw threads contacting the half-nut block.

The half-nut block also includes a cam which can be engaged by a cam block mounted in a lever positioned in the arm to force the half-nut block to disengage its threaded first bore from contact with the lead screw and move its second, larger bore about the lead screw. When the second bore is positioned about the lead screw, the traveler mechanism can be re-positioned along the lead screw as desired. A second biasing system is used to assist re-engagement of the threads of the first bore with the threads of the lead screw. This second system, in one embodiment, comprises a spring contacting the half-nut block opposite the cam. The spring opposes this lever/cam block movement of the half-nut cam and when the lever is released, the spring forces the half-nut block threads to re-engage the lead screw threads.

Additionally, a stop arrangement is used to oppose disengagement of the half-nut block from the lead screw in the case where an undesired external force is applied. In one embodiment, the half-nut block comprises a protrusion into which are formed a flat surface used as a stop and the cam. The bearing block into which the half-nut block is mounted includes a striker plate which the stop would engage in the case where the external undesired force is applied. The flat face of the protrusion (stop) will engage the striker which will thereby limit the movement of the half-nut block to prevent disengagement from the lead screw. In order to use the lever/cam block arrangement to disengage the half-nut block from the lead screw, the cam block of the lever causes rotation of the half-nut block so that the stop is not aligned with the striker. Further pressure by the cam block then causes half-nut block disengagement.

In accordance with another aspect of the invention, the traveler mechanism is non-rigidly coupled to the arm through bearing surfaces. In one embodiment, the traveler mechanism includes a bearing surface normal to the lead screw. The arm includes a surface also normal to the lead screw and in which are mounted two bearings, in one embodiment. These bearings are used to engage the traveler mechanism's bearing surface. The arm bearings are located at points on the traveler mechanism where transmission of any wobbling of the traveler mechanism to the arm is reduced. The rotation of the lead screw causes the traveler mechanism to move against the arm bearings thereby imparting the linear motion to the arm. Because the only contact with the arm is the bearings, transmission of wobbling of the traveler mechanism to the arm due to imperfections in the lead screw will be reduced. Only the forward linear motion of the traveler will be coupled to the arm.

The above and other objects and advantages of the present invention will become apparent from the following more detailed description, when taken in conjunction with the accompanying drawings of an illustrative embodiment.

BRIEF DESCRIPTION OF THE DRAWINGS

FIG. 1 is a perspective view, partially broken away, illustrating a syringe infusion pump having an engagement/disengagement and a decoupling mechanism embodying the principles of the present invention;

FIG. 3 is a partial cross-sectional view of FIG. 2 showing the lead screw engaged with the threaded bore of the half-nut block;

FIG. 4 is a view of a half-nut block engaging a lead screw and a wear plate;

DETAILED DESCRIPTION OF THE PREFERRED EMBODIMENT

Figure 5:
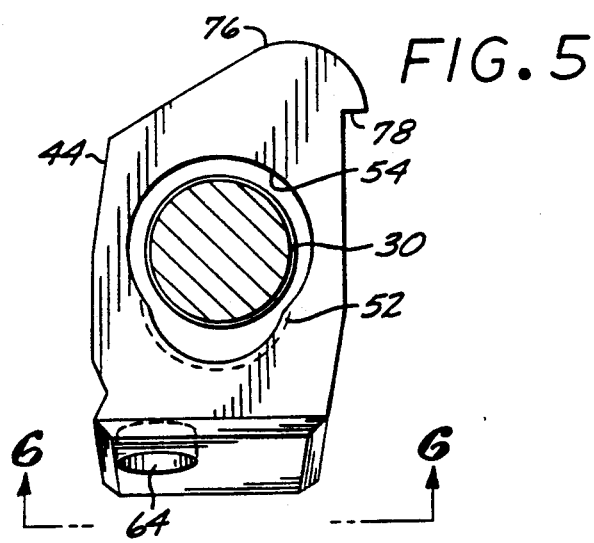
FIG. 5 is also a side section view of the half-nut block taken at 5—5 of FIG. 4 but the lead screw is positioned so that it is centered in the larger, unthreaded bore.

Referring now with more particularity to the drawings for the purpose of illustrating the presently preferred embodiment of the present invention, there is shown a syringe infusion pump indicated generally by reference numeral 10.

Although reference is made herein to the intravenous administration environment, and particularly to syringe pumps, it is to be understood that this is by way of example only, and the apparatus as set forth in the ensuing description is suitable for use in other environments and for a wide variety of applications other than intravenous administration.

Mounted in the infusion pump 10 shown in FIG. 1 is a syringe 12, comprising a body 14 and a plunger 16. The plunger 16 is coupled at its extremity to an arm 18 forming part of the pump 10. The arm 18 moves the plunger towards the syringe body 14 so as to expel the contents of the syringe. The syringe mounting arrangement includes a trough 20 in which the syringe body 14 is placed and a detent 22 in which the extended rim of the syringe body is placed. The detent cooperates with a syringe mounting arm 24 to hold the syringe body 14 stationary while in the pump 10. The thumbrest 26 of the plunger 16 is coupled to the pump arm 18 such as by the slot means shown in FIG. 1. The arm 18 contains a slot 28 into which is fitted the thumbrest 26 of the particular syringe to be used. When the thumbrest is fitted into the slot, vertical motion of the arm is inhibited.

The pump 10 includes a lead screw 30 shown in the partially broken-away view of FIG. 1. As will be described in more detail below, a traveler mechanism 32 is mounted to the lead screw 30 and converts the rotary motion of the lead screw to linear motion. The pump arm 18 is coupled to the traveler mechanism 32 to communicate the linear motion of the traveler mechanism to the syringe plunger 16. Shown on both sides of the traveler mechanism are bellows 34. These bellows function to keep dust and dirt from entering the mechanism and to add torsional resistance to vertical movement of the arm 18 to tend to force the arm to return to its "engaged" position. The traveler mechanism 32 is mounted on a C-tube 36 which is disposed parallel to the lead screw 30 and surrounds it except for the longitudinal opening of the C-tube which in this embodiment, is located such that it faces rearward in relation to the pump 10. Both the C-tube 36 and lead screw 30 are mounted at one end to the end mount 38. The lead screw 30 is engaged with a motor and drive gears mechanism 40 at its other end which are used for imparting rotary motion to the lead screw 30. Lead screw drive motor/gear arrangements are well known to those skilled in the art and no further detail of such is provided herein. The C-tube 36 is also mounted at its other end to a second end mount located within the motor and drive gears mechanism shown generally by numeral 40.

Figure 2:
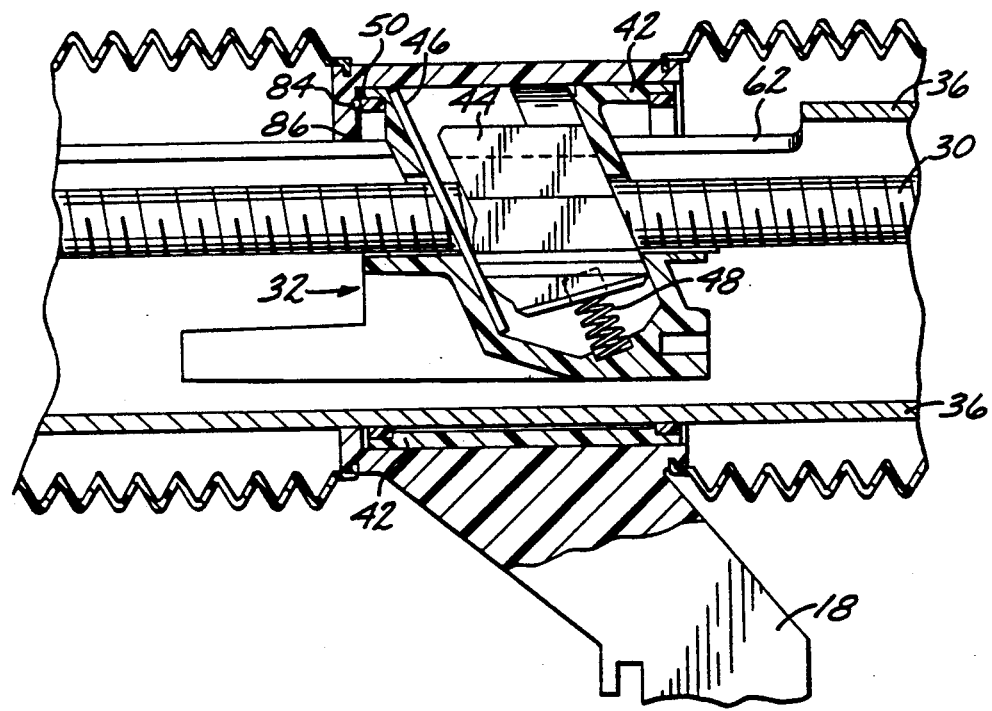
FIG. 2 is a top, partially cut-away view showing the arm, C-tube, decoupling mechanism, bearing block and half-nut block used in an embodiment in accordance with the principles of the invention.

Referring now to FIG. 2, the traveler mechanism 32 is shown as comprising a bearing block 42, a half-nut block 44, a wear plate 46, a spring 48, and a bearing surface 50. As shown, the traveler mechanism 32 is mounted on the C-tube 36 and the lead screw 30. In particular, the half-nut block 44; which is mounted within the bearing block 32, is engaged with the lead screw 30.

Referring now to FIG. 3, the half-nut block 44 includes two bores. The first bore 52 is threaded while the second bore 54 has no threads. The second bore 54 is disposed at a position offset from but overlapping the first bore 52 and is larger than both the first bore 52 and the lead screw 30. The offset but overlapping position of the second bore 54 results in the first threaded bore 52 being effectively a half-nut. The half-nut block 44 has an engaged position and a disengaged position. The half-nut block 44 is engaged when the threads of the first bore 52 are in engagement with the threads of the lead screw 30 as is shown in FIG. 3. The half-nut block 44 is disengaged when the second bore 54 surrounds the lead screw 30, as shown in FIG. 5, thus permitting the traveler mechanism 32 to be positioned along the lead screw 30 as desired.

Referring now to FIG. 4, the half-nut block 44 in this embodiment has an exterior rounded surface with a bearing surface 60 located thereon which is the point of contact with a wear plate 46. A tangent to this bearing surface (on which the wear plate is lying in FIG. 4) is perpendicular to the line 45 drawn through the center 47 of the half-nut block 44 threaded surface area along the bottom edge of the lead screw 30. The use of this point as the bearing point has been found to minimize thread wear and stresses because the driving forces are more evenly distributed across all of the threads engaged by the half-nut block 44. The half-nut block 44 is shown in FIG. 4 as having a surface 56 parallel to the tangent. The angle is indicated generally by numeral 58. In one embodiment, this angle was approximately 67°. This angle included the angle of the threads and an additional amount required to overcome the frictional forces between the wear plate 46 and the half-nut block 44. In the embodiment shown, the wear plate 46 is mounted rigidly in the bearing block 42, has the same acute angle 58 as the half-nut block 44 and provides a bearing surface with which the half-nut block 44 engages when the lead screw 30 rotates.

As shown in FIG. 2, the half-nut block 44 is mounted inside the bearing block 42. The bearing block 42 is slidably mounted on the C-tube 36, the C-tube being located so as to surround the lead screw 30 and be parallel therewith along the length of the lead screw to be used for moving the arm 18. The opening 62 of the "C" of the C-tube is shown facing rearward in the embodiment shown in FIG. 2. As further shown in FIG. 2, part of the bearing block 42 extends out the opening of the C-tube 36. This arrangement prevents the bearing block 42 and the half-nut block 44 from rotating along with the rotation of the lead screw 30.

Figure 6:
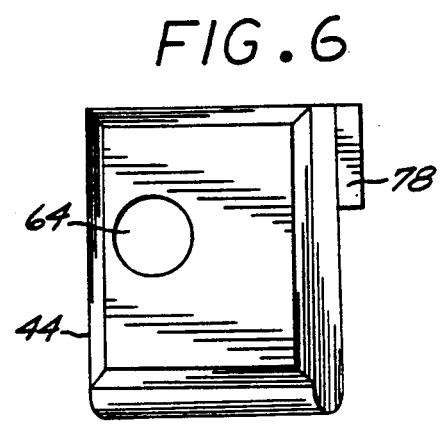
FIG. 6 is an end-on view of the half-nut block showing a recess for containing the end of a spring.

By disposing the wear plate 46 at an acute angle to the half-nut block 44 and mounting it rigidly within the bearing block 42 which can only move in a direction parallel to the lead screw 30, rotation of the lead screw 30 will cause a force to be developed in the half-nut block 44 into the threads of the lead screw 30. This force will tend to drive the half-nut block 44 into closer contact with the lead screw 30. This arrangement thus results in a biasing system. During periods of non-rotation of the lead screw 30, the spring 48 biases the threads of the half-nut block 44 into contact with the threads of the lead screw 30. However, it has been found that the force of the spring 48 need not be as great as in prior techniques due to the angled arrangement of the half-nut block 44 as described above. FIGS. 5 and 6 show a recess 64 formed into the half-nut block 44 into which is disposed the spring 48. At its other end, spring 48 is engaged with an internal surface of the bearing block 42.

Figure 7:
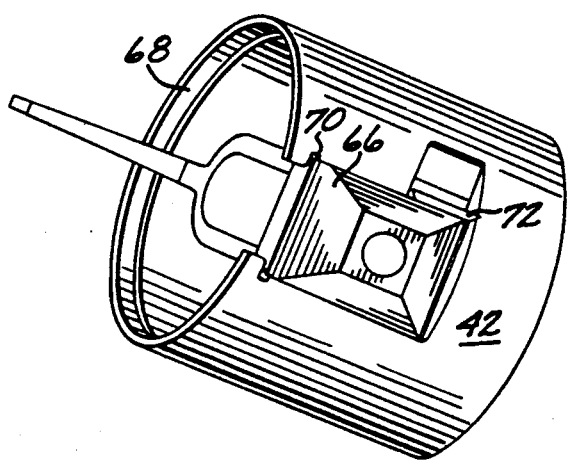
FIGS. 7, 8, and 9 are a perspective view, top view, and cross-sectional end-on view respectively of a bearing block usable in accordance with the principles of the invention.
Figure 8:
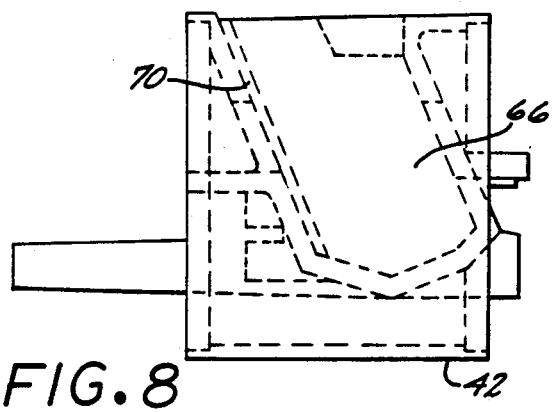

FIGS. 7 and 8 show further detail of the bearing block 42. In FIG. 7, the recess 66 for the half-nut block 44 is shown. Also shown is the enlarged diameter 68 of the bearing block 42 at one end in which a bearing may be mounted. This bearing facilitates the sliding of the bearing block along the C-tube 36. Such a bearing may be mounted at each end of the bearing block 42. Also shown is a slot 70 for mounting the wear plate in the bearing block and a slot 72 for mounting the striker.

FIG. 8 presents a side view showing the recesses in phantom lines. Shown is the recess 66 for the half-nut block 44 and the slot 70 for mounting the wear plate 46.

Figure 9:
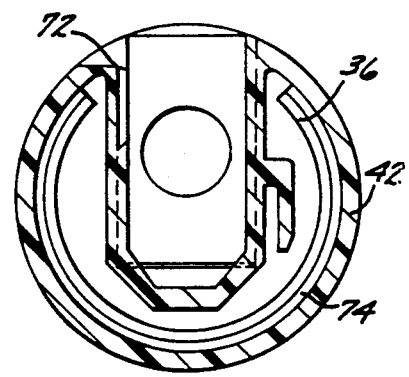

FIG. 9 is a cross-sectional end-on view showing the mounting of the bearing block 42 on the C-tube 36. A bearing 74 is shown between the bearing block 42 and the C-tube 36. Also shown is the slot 72 for mounting the striker. Because a portion of the bearing block protrudes through the opening of the C-tube 36, the bearing block 44 cannot rotate with the rotation of the lead screw 30 and can only move in a direction parallel to the lead screw.

Figure 10:
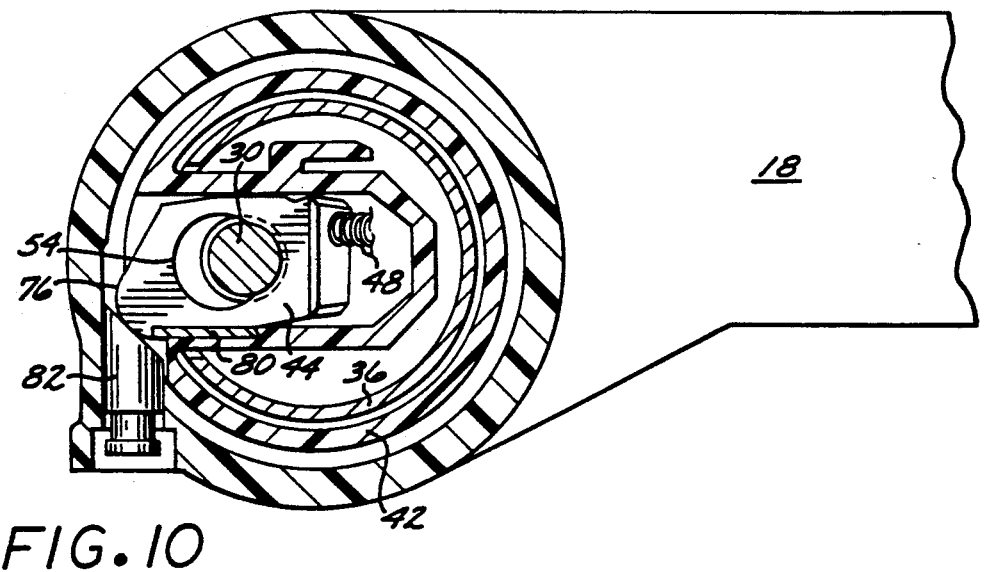

Referring once again to FIGS. 3, 5, and 6, the half-nut block 44 includes a protrusion having a cam 76 and a stop 78 formed thereon. The stop 78 is used to engage a striker 80 as shown in FIG. 10. By this arrangement, the half-nut block 44 is prevented from disengaging from the lead screw should a force be applied to the area of the half-nut block 44 located at the rear of the pump 10. In the engaged mode, the stop 78 is not in contact with the striker 80 although they are located adjacent one another. If the undesired force is applied which would cause the half-nut block 44 to move up or in, the stop 78 will contact the striker 80 and such force will be resisted.

Figure 11:
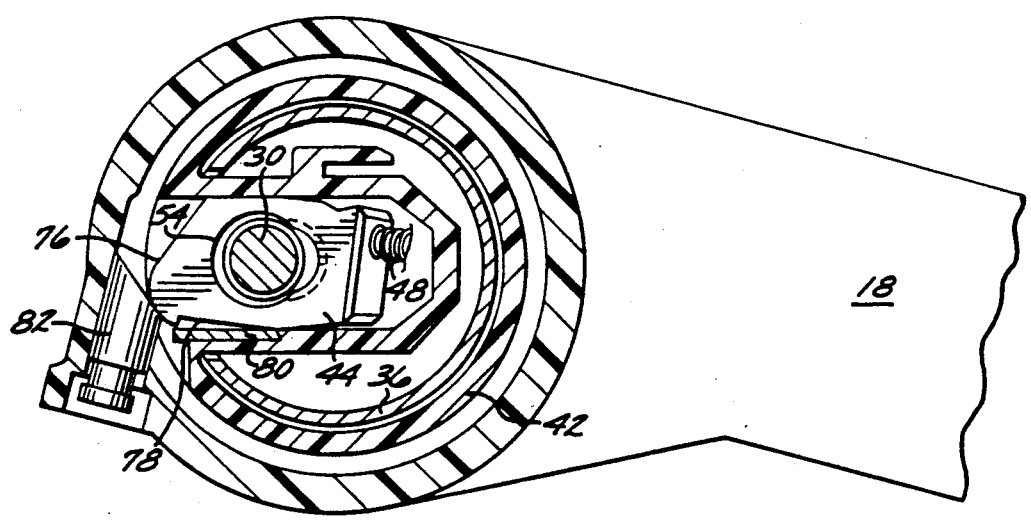
FIGS. 10 and 11 are views showing an embodiment of the invention wherein rotation of the arm causes disengagement of the half-nut block from the lead screw.

Referring now to FIGS. 10 and 11, the use of the arm to disengage the half-nut block 44 from the lead screw 30 is presented. As shown, the arm includes a cam block 82 rigidly mounted in the arm 18 at the backside of the pump 10. The cam block 82 engages the cam 76 of the half-nut block 44 when the arm 18 is rotated downward. The cam block 82 causes the half-nut block 44 to be rotated somewhat upward so that the stop 78 disengages from the striker plate 80. Further motion of the arm 18 then causes the half-nut block 44 to be pushed inward against the spring 48. The action of pushing the half-nut block 44 inward causes it to disengage from the threads of the lead screw 30 and move the second bore 54 around the lead screw 30 thus terminating contact with the lead screw. Due to this disengagement, the traveler mechanism 32 may be moved along the lead screw 30 as desired. Movement of the traveler mechanism along the lead screw is typically accomplished by moving the arm 18 in the desired direction. To reengage, the arm is rotated upward thus relieving the pressure on the cam 76. The compressed spring 48 will expand and force the half-nut block 44 back to its original position so that the first bore threads engage the threads of the lead screw 30. Because the spring is mounted off center to the half-nut block 44 (see FIG. 6), the spring 48 will cause a rotation of the half-nut block 44 so that the stop 78 will once again be aligned with the striker plate 80.

Referring again to FIG. 10, it can be seen that the arm 18 surrounds the C-tube 36 and in this embodiment, the bearing block 44 also. Referring now to FIG. 2, it can be seen that although the arm 18 surrounds the bearing block 44, and therefore the C-tube 36, it does not rest on the bearing block 44. The arm 18 actually is slidably mounted on the C-tube at either end of the bearing block 44. The means for transmitting the linear movement of the bearing block 44 due to lead screw 30 rotation to the arm 18 is through a particular point or points of contact on the traveler mechanism 32. As discussed above, various imperfections in the lead screw may cause the traveler mechanism 32 to wobble or otherwise move unsmoothly. It is believed that non-rigidly coupling the arm to the traveler mechanism 32 in this manner has the effect of transmitting only the linear motion of the traveler mechanism 32 to the arm 18 and reducing the transmission of the undesired motion. In one embodiment, such coupling was accomplished through the use of a pair of metallic bearings (one of which is shown by numeral 84) such as pins with rounded heads, mounted in the outside surface 86 of the bearing block 18 which faces the arm. The bearing surface 50 of the arm 18 engages the bearings 84 to transmit the linear motion of the bearing block to the arm 18. These bearings were located on the bearing block surface 86 at points which were 5.08 mm (0.2 inches) forward of a vertical centerline of the C-tube 36.

It will be apparent from the foregoing that, while particular forms of the invention have been illustrated and described, various modifications can be made without departing from the spirit and scop of the invention. Accordingly, it is not intended that the invention be limited, except as by the appended claims.

What is claimed is:

1. An apparatus for converting the rotational motion of a threaded lead screw into linear motion, the apparatus comprising:
    half-nut means having threads for engaging the threads of the lead screw around a predetermined arc thereof and traveling along the lead screw in a first direction in response to rotation of the lead screw, the half-nut means comprising a bearing surface protruding in the first direction;
    mounting means for providing a mounting surface parallel with the lead screw and along a predetermined extent of the lead screw length;
    block means for moving along the mounting means in response to the traveling of the half-nut means along the lead screw, the block means comprising a surface disposed at an acute angle to the longitudinal axis of the lead screw, the angled surface contacting the bearing surface of the half-nut means for urging the threads of the half-nut means into contact with the threads of the lead screw during rotation of the lead screw; and
    biasing means for urging the half-nut means into contact with the lead screw during periods of rotation and non-rotation of the lead screw.

2. The apparatus of claim 1 further comprising disengaging means for disengaging the threads of the half-nut means from the threads of the lead screw so that the half-nut means may be moved to a selected position along the lead screw.

3. The apparatus of claim 2 wherein the disengaging means comprises
    a cam disposed on the half-nut means, and
    lever means for engaging the cam and causing the threads of the half-nut means to disengage from the threads of the lead screw; and
    the biasing means is also for opposing the action of the lever to disengage the half-nut means from the lead screw and urging the threads of the half-nut means into re-engagement with the threads of the lead screw upon relaxation of the lever means.

4. The apparatus of claim 2 further comprising stop means for preventing the disengagement of the threads of the half-nut means from the threads of the lead screw other than by use of the disengagement means.

5. The apparatus of claim 1 wherein:
    the half-nut means completely surrounds the lead screw and comprises two bores, the first bore being threaded for engagement with the threads of the lead screw threads and the second bore being larger than the lead screw and overlapping the first bore so that the first bore includes an arc of no greater than 180°.

6. The apparatus of claim 1 wherein the mounting means comprises engagement means for engaging the block means such that rotation of the block means is opposed.

7. The apparatus of claim 6 wherein the mounting means comprises a tube on which the block means slides in response to traveling of the half-nut means along the lead screw.

8. The apparatus of claim 1 wherein the angle of the angled surface on the block means is greater than the angle of the threads of the lead screw.

9. The apparatus of claim 1 wherein the half-nut means also comprises a surface formed on the half-nut which is disposed at an acute angle to the longitudinal axis of the lead screw, the angle being approximately equal to the angle of the angled surface of the block means.

10. The apparatus of claim 1 further comprising an arm coupled to the block means for transmitting the linear motion of the block means to a remote location.

11. The apparatus of claim 10 wherein the arm is coupled to the block means by at least one bearing means.

12. The apparatus of claim 11 wherein the arm is coupled to the block means at two points by bearing means for providing a bearing surface at each point.

13. The apparatus of claim 10 further comprising disengaging means for disengaging the threads of the half-nut means from the threads of the lead screw so that the half-nut means may be moved to a selected position along the lead screw, the disengaging means comprising:
    a cam disposed on the half-nut means;
    lever means disposed within the arm for engaging the cam and causing the threads of the half-nut means to disengage from the threads of the lead screw upon rotating the arm; and
    the biasing means is also for opposing the action of the lever to disengage the half-nut means from the lead screw and for urging the threads of the half-nut means into re-engagement with the threads of the lead screw upon relaxation of the lever means.

14. The apparatus of claim 13 wherein the stop means comprises:
    a protrusion having a substantially flat surface formed on the half-nut means; and a striker disposed in the block means for engaging the flat surface of the protrusion to oppose movement of the half-nut means.

15. The apparatus of claim 14 further comprising:
an arm coupled to the block means for transmitting the motion of the block means to a remote location;
wherein the disengaging means comprising:
a cam disposed on the half-nut means;
lever means disposed within the arm for engaging the cam and overcoming the stop means and for causing the threads of the half-nut means to disengage from the threads of the lead screw upon rotating the arm; and
the biasing means for urging the cam back into position to re-align the flat surface with the striker and for urging the threads of the half-nut means into re-engagement with the threads of the lead screw upon relaxation of the lever means.

16. In a syringe pump, a combination comprising:
a threaded lead screw;
half-nut means having threads for engaging the threads of the lead screw around a predetermined arc thereof and traveling along the lead screw in a first direction in response to rotation of the lead screw, the half-nut means comprising a bearing surface protruding in the first direction;
mounting means for providing a mounting surface parallel with the lead screw and along a predetermined extent of the lead screw length;
block means for moving along the mounting means in response to the traveling of the half-nut means along the lead screw and for engaging the block means such that rotation of the block means is opposed, the block means comprising a surface disposed at an acute angle to the longitudinal axis of the lead screw, the angled surface contacting the bearing surface of the half-nut means for urging the threads of the half-nut means into contact with the threads of the lead screw during rotation of the lead screw;
biasing means for urging the half-nut means into contact with the lead screw during periods of rotation and non-rotation of the lead screw;
an arm coupled to the block means for transmitting the motion of the block means to a remote location; and
disengaging means coupled to the arm for disengaging the threads of the half-nut means from the threads of the lead screw so that the half-nut means may be moved to a selected position along the lead screw.

17. The combination of claim 16 wherein the half-nut means completely surrounds the lead screw and comprises two bores, the first bore being threaded for engagement with the threads of the lead screw threads and the second bore being larger than the lead screw and overlapping the first bore so that the first bore includes an arc of no greater than 180°.

18. The combination of claim 17 wherein:
the angle of the angled surface on the block means is greater than the angle of the threads of the lead screw; and
the half-nut means comprises a surface on which the bearing surface is formed which is disposed at an acute angle to the longitudinal axis of the lead screw, the angle being approximately equal to the angle of the angled surface of the block means.

19. The combination of claim 16 wherein: the disengaging means comprising
a cam disposed on the half-nut means and
lever means disposed within the arm for engaging the cam and causing the threads of the half-nut means to disengage from the threads of the lead screw upon rotating the arm; and
the biasing means is also for urging the threads of the half-nut means into reengagement with the threads of the lead screw upon relaxation of the lever means.

20. The combination of claim 16 further comprising stop means for preventing the disengagement of the half-nut from the lead screw other than by use of the disengagement means.

21. The combination of claim 20 wherein the stop means comprises:
a protrusion having a substantially flat surface formed on the half-nut means; and
a striker disposed in the block means for engaging the flat surface of the protrusion to oppose movement of the half-nut means.

22. The combination of claim 21 wherein:
the half-nut means comprises a cam;
the arm comprises lever means for engaging the cam and overcoming the stop means and for causing the threads of the half-nut means to disengage from the threads of the lead screw upon rotating the arm; and
the biasing means is also for urging the cam back into position to re-align the flat surface with the striker and for urging the threads of the half-nut means into reengagement with the threads of the lead screw upon relaxation of the lever means.

23. The combination of claim 16 wherein the arm is coupled to the block means by at least one bearing means.

24. The combination of claim 23 wherein the arm is coupled to the block means at two points by bearing means for providing a bearing surface at each point.

25. In a syringe pump, the combination comprising:
a threaded lead screw;
half-nut means having threads for engaging the threads of the lead screw and for traveling along the lead screw in a first direction in response to rotation of the lead screw, the half-nut means comprising a bearing surface protruding in the first direction, the half-nut means completely surrounding the lead screw and comprising two bores, the first bore being threaded for engagement with the threads of the lead screw threads and the second bore being larger than the lead screw and overlapping the first bore so that the first bore includes an arc of no greater than 180°;
mounting means for providing a mounting surface parallel with the lead screw and along a predetermined extent of the lead screw length;
block means for moving along the mounting means in response to the traveling of the half-nut means along the lead screw, the block means comprising a surface disposed at an acute angle to the longitudinal axis of the lead screw, the angled surface contacting the bearing surface of the half-nut means for urging the threads of the half-nut means into contact with the threads of the lead screw during rotation of the lead screw;
an arm coupled to the block means for transmitting the motion of the block means to a remote location;

disengaging means coupled to the arm for disengaging the threads of the half-nut means from the threads of the lead screw so that half-nut means may be moved to a selected position along the lead screw, the disengaging means comprising:

a cam disposed on the half-nut means;

lever means disposed within the arm for engaging the cam and causing the threads of the half-nut means to disengage from the threads of the lead screw upon rotating the arm; and biasing means for urging the threads of the half-nut means into contact with the threads of the lead screw during periods of rotation and nonrotation of the lead screw.

26. The combination of claim 25 wherein the arm is coupled to the block means by at least one bearing means.

27. The combination of claim 26 wherein the arm is coupled to the block means at two points by bearing means for providing a bearing surface at each point.

* * * * *